US00PP20717P2

(12) United States Plant Patent
Moonen

(10) Patent No.: US PP20,717 P2
(45) Date of Patent: Feb. 2, 2010

(54) ***GAILLARDIA* PLANT NAMED 'KIEGALPEA'**

(50) Latin Name: *Gaillardia aristata*
Varietal Denomination: KIEGALPEA

(75) Inventor: Carla M. Moonen, Enkhuizen (NL)

(73) Assignee: Florensis Hamer CS, Hendrik Ido Ambacht (NL)

( * ) Notice: Subject to any disclaimer, the term of this patent is extended or adjusted under 35 U.S.C. 154(b) by 0 days.

(21) Appl. No.: 12/313,082

(22) Filed: Nov. 17, 2008

(51) Int. Cl.
*A01H 5/00* (2006.01)

(52) U.S. Cl. ..... Plt./431

(58) Field of Classification Search ..... Plt./431
See application file for complete search history.

*Primary Examiner*—Kent L Bell
(74) *Attorney, Agent, or Firm*—Jondle & Associates, P.C.

(57) ABSTRACT

'KIEGALPEA' is a new *Gaillardia* plant particularly distinguished by having uniform, yellow inflorescences with an orange ring and a uniform, compact plant habit, is disclosed.

1 Drawing Sheet

Genus and species: *Gaillardia aristata.*
Variety denomination: 'KIEGALPEA'.

BACKGROUND OF THE INVENTION

The present invention comprises a new and distinct cultivar of *Gaillardia*, botanically known as *Gaillardia aristata*, and hereinafter referred to by the cultivar name 'KIEGALPEA'. 'KIEGALPEA' originated from a cross conducted in May 2004 in a cultivated field in Venhuizen, The Netherlands. The female parent was a proprietary unnamed *Gaillardia* plant (unpatented) with bicolor light-yellow and light-orange inflorescences. The male parent was a proprietary unnamed *Gaillardia* plant (unpatented) having inflorescences with a yellow-orange ring.

The new cultivar was created in the spring of 2004 in Venhuizen, The Netherlands and has been asexually reproduced repeatedly by vegetative cuttings in Venhuizen, The Netherlands over a three year period. 'KIEGALPEA' has been found to retain its distinctive characteristics through successive asexual propagations.

Plant Breeder's Rights for this cultivar were applied for in Europe in September 2008. 'KIEGALPEA' has not been made publicly available more than one year prior to the filing of this application.

SUMMARY OF THE INVENTION

The following are the most outstanding and distinguishing characteristics of this new cultivar when grown under normal horticultural practices in Venhuizen, The Netherlands.

1. Uniform, yellow inflorescences with an orange ring; and
2. Uniform and compact plant habit.

DESCRIPTION OF THE PHOTOGRAPH

This new *Gaillardia* plant is illustrated by the accompanying photograph which shows the plant's form, foliage and inflorescences. The colors shown are as true as can be reasonably obtained by conventional photographic procedures. The photograph is of a plant approximately 4 to 5 months old in the spring/summer.

DESCRIPTION OF THE NEW CULTIVAR

The following detailed description sets forth the distinctive characteristics of 'KIEGALPEA'. The data which define these characteristics were collected from asexual reproductions carried out in Venhuizen, The Netherlands. The detailed description was taken from 4 to 5 month-old plants grown in a cultivated field, under natural light in the spring/summer. Color references are to the R.H.S. Colour Chart of The Royal Horticultural Society of London (R.H.S.), 1986 Edition.

DETAILED BOTANICAL DESCRIPTION

Classification:
- *Family.*—Asteraceae.
- *Botanical name.*—*Gaillardia aristata.*
- *Common name.*—Blanket flower.

Parentage:
- *Female.*—Unnamed *Gaillardia* plant (unpatented) with bicolor light-yellow and light-orange inflorescences.
- *Male.*—Unnamed *Gaillardia* plant (unpatented) having inflorescences with a yellow-orange ring.

Plant description:
- *Appearance, form or habit.*—Compact, upright.
- *Growth and branching habit.*—Fast; base branching.
- *Height (from top of soil).*—25 cm.
- *Width (including inflorescences).*—25 cm.
- *Time to produce a finished plant having inflorescences.*—80–100 days.
- *Time to initiate and develop roots.*—10–12 days.
- *Root description.*—White; well-spread and developed.

Leaves:
- *Arrangement.*—Alternate and opposite.
- *Shape.*—Lanceolate.
- *Apex.*—Ovate.
- *Base.*—Rounded.
- *Margin.*—Entire.
- *Immature leaf color.*—Upper surface: RHS 137A Lower surface: RHS 137B.
- *Mature leaf color.*—Upper surface: RHS 137A Lower surface: RHS 137B.
- *Length.*—8 cm to 10 cm.
- *Width.*—2.5 cm to 3.5 cm.

*Texture.*—Upper surface: Pubescent Lower surface: Slightly pubescent.
*Venation pattern.*—Reticulate.
*Venation color.*—Upper surface: RHS 137A and RHS 137B (light-green) Lower surface: RHS 137C (light-green).
*Petioles.*—Absent.

Stems:
*Average number of branches per plant.*—About 15.
*Length.*—20 cm.
*Diameter.*—0.4 cm.
*Internode length.*—2.0 cm to 4.0 cm.
*Shape.*—Round.
*Color.*—RHS 138C (green).
*Texture.*—Pubescent.

Inflorescence buds:
*Shape.*—Round.
*Length.*—0.8 cm.
*Diameter.*—1.5 cm to 2.0 cm.
*Color* (*general*).—In center: Yellow-green At margin: Yellow.
*Texture.*—Pubescent.

Inflorescence:
*Appearance or form.*—Disc and ray florets develop acropetally on a captiulum.
*Type.*—Composite, single-flowered.
*Blooming habit* (*flowering season*).—Constant, no flushes.
*Average quantity of inflorescences per plant.*—10 to 15.
*Lastingness of the inflorescences on the plant.*—10 days to 14 days.
*Fragrance.*—None.
*Inflorescence diameter.*—6.0 cm to 7.0 cm.
*Inflorescence depth* (*height*).—1.5 cm to 2.0 cm.
*Disc diameter.*—3.5 cm.
*Receptical.*—Shape: Hemispherical Diameter: 3.0 cm to 4.0 cm Depth: 1.5 cm Color: RHS 162A (honey-yellow).

Disc florets:
*Average quantity per inflorescence.*—About 100.
*Shape.*—Linear.
*Apex.*—Tridentate.
*Base.*—Attenuate.
*Margin.*—Entire.
*Length.*—1.0 cm.
*Diameter* (*at apex*).—0.3 cm.
*Diameter* (*at base*).—0.1 cm.
*Texture.*—Smooth.
*Color* (*general*).—Apex: Green-yellow Center: Yellow Base: Green.

Ray floret:
*Average quantity per inflorescence.*—14 to 16.
*Length.*—3.0 cm.
*Width.*—1.5 cm.
*Shape.*—Denticulate.
*Apex.*—Tridentate.
*Base.*—Attenuate.
*Margin.*—Entire.
*Texture* (*both surfaces*).—Smooth.
*Color, when opening* (*both surfaces*).—Bicolor; RHS 13B (yellow) and RHS 24C (orange).
*Color, fully opened* (*both surfaces*): RHS 13A (yellow) with an RHS 24B (orange) ring.
*Peduncle.*—Length: 10 cm to 12 cm Diameter: 0.2 cm to 0.3 cm Texture: Pubescent Color: RHS 138C (green).

Involucral bracts:
*Average quantity.*—1 per disc floret.
*Shape.*—Lanceolate.
*Aspect.*—Upright.
*Length.*—1.1 cm.
*Width.*—0.3 cm.
*Apex.*—Denticulate.
*Base.*—Rounded.
*Margin descriptor.*—Entire.
*Texture.*—Pubescent.

Reproductive organs:
*Androecium.*—Location: Middle (in disc floret) Stamens: Quantity: 80 to 100 Shape: Long, bended Filament: Length: 0.8 cm Diameter: 0.1 cm Anther: Shape: V-shaped Length: 1.0 cm to 1.5 cm Diameter: 0.1 cm Pollen: Color: RHS 15B (yellow) Amount: Moderate.
*Gynoecium.*—Pistils Number: 1 per ray floret Length: 0.4 cm to 0.5 cm Diameter: 0.1 cm Stigma: Shape: Round Length: 0.2 cm Diameter: 0.1 cm Style: Shape: Long and 2-parted Length: 1.0 cm Diameter: 0.1 cm Ovary length: 0.2 cm.

Fruit/seed set: Composite seeds; light-brown to transparent in color; achene shape and 0.9 cm in diameter Disease and insect resistance: No specific disease resistance but tolerant to mildew

COMPARISON WITH PARENTAL LINES AND KNOWN CULTIVAR

'KIEGALPEA' is distinguished from its parents mainly by inflorescence color. The unnamed female parent has bi-colored light-yellow and light-orange inflorescences and the unnamed male parent has inflorescences with a yellow-orange ring. 'KIEGALPEA' has yellow inflorescences with an orange ring.

'KIEGALPEA' is distinguished from the commercial variety 'Granada' (unpatented) by having a more compact plant habit when compared to 'Granada'. 'KIEGALPEA' has a more uniform inflorescence color pattern, while 'Granada' has more shading in its inflorescence color pattern.

I claim:

1. A new and distinct cultivar of *Gaillardia* plant as shown and described herein.

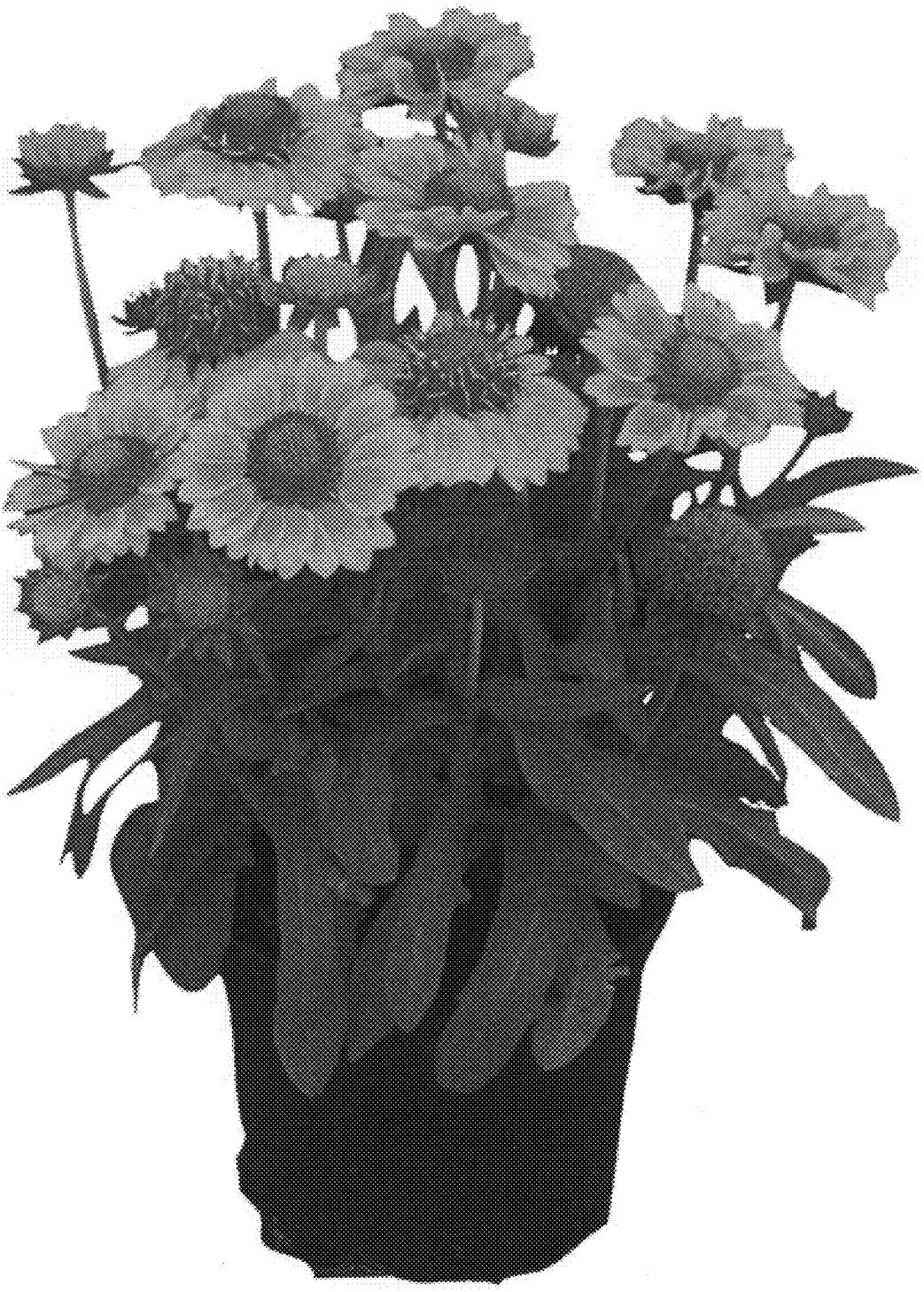

* * * * *